US010366645B2

(12) United States Patent
Wang et al.

(10) Patent No.: US 10,366,645 B2
(45) Date of Patent: Jul. 30, 2019

(54) LIGHTING-ON DEVICE AND METHOD FOR CELL TEST

(71) Applicants: BOE TECHNOLOGY GROUP CO., LTD., Beijing (CN); Fuzhou BOE Optoelectronics Technology Co., Ltd., Fujian (CN)

(72) Inventors: Yong Wang, Beijing (CN); Jaeyoung Joo, Beijing (KR); Hongyan Guo, Beijing (KR); Yo Seop Cheong, Beijing (KR); Yang Yu, Beijing (CN); Zongtian Xie, Beijing (CN); Zengyang Jiang, Beijing (CN); Cundui Tang, Beijing (CN); Lingling Fan, Beijing (CN); Huailiang Wu, Beijing (CN)

(73) Assignees: BOE TECHNOLOGY GROUP CO., LTD., Beijing (CN); FUZHOU BOE OPTOELECTRONICS CO., LTD., Fujian (CN)

( * ) Notice: Subject to any disclaimer, the term of this patent is extended or adjusted under 35 U.S.C. 154(b) by 48 days.

(21) Appl. No.: 15/846,408

(22) Filed: Dec. 19, 2017

(65) Prior Publication Data

US 2018/0247578 A1 Aug. 30, 2018

(30) Foreign Application Priority Data

Feb. 28, 2017 (CN) .......................... 2017 1 0111937

(51) Int. Cl.
*G02F 1/13* (2006.01)
*G06T 7/33* (2017.01)
(Continued)

(52) U.S. Cl.
CPC ............. *G09G 3/006* (2013.01); *G01B 11/14* (2013.01); *G01N 21/95* (2013.01); *G02F 1/1309* (2013.01);
(Continued)

(58) Field of Classification Search
CPC ........... G01N 2021/9513; G01N 21/95; G01B 11/14; G01J 1/44; G02F 1/1303;
(Continued)

(56) References Cited

U.S. PATENT DOCUMENTS 5,691,764 A * 11/1997 Takekoshi .............. G09G 3/006 348/125
6,137,300 A * 10/2000 Hayashida ........... G01R 1/0408 324/750.18
(Continued)

FOREIGN PATENT DOCUMENTS

JP 10019731 A * 1/1998 ............. G01N 21/95
WO WO 2019019060 * 1/2019

*Primary Examiner* — Gordon J Stock, Jr.
(74) *Attorney, Agent, or Firm* — Calfee, Halter & Griswold LLP

(57) ABSTRACT

The present disclosure provides a lighting-on device and a method for cell test. The lighting-on device includes a movable unit including a first marker; an image acquisition unit configured to acquire an image indicating an actual relative positional relationship between the first marker and a second marker on a display panel; a calculation unit configured to calculate the actual relative positional relationship between the first marker and the second marker according to the image; a first position adjustment unit configured to drive the movable unit so as to adjust the actual relative positional relationship; and a first control unit configured to determine whether the adjusted actual relative positional relationship has been aligned by the first position adjustment unit according to the relative positional relationship between the first marker and the second marker.

14 Claims, 8 Drawing Sheets

(51) Int. Cl.
*G06T 7/73* (2017.01)
*G09G 3/00* (2006.01)
*G01B 11/14* (2006.01)
*G01N 21/95* (2006.01)

(52) U.S. Cl.
CPC .................. *G06T 7/33* (2017.01); *G06T 7/74* (2017.01); *G01N 2021/9513* (2013.01); *G06T 2207/30121* (2013.01); *G06T 2207/30204* (2013.01); *G09G 2300/04* (2013.01)

(58) Field of Classification Search
CPC ......... G02F 1/1309; G06T 2207/30121; G06T 2207/30204; G06T 7/33; G06T 7/74; G09G 2300/04; G09G 3/006
See application file for complete search history.

(56) References Cited

U.S. PATENT DOCUMENTS

| | | | | |
|---|---|---|---|---|
| 8,492,739 | B2 * | 7/2013 | Choi | G01J 1/08 250/226 |
| 9,546,864 | B2 * | 1/2017 | Luo | G01B 11/27 |
| 9,761,183 | B2 * | 9/2017 | Yang | G09G 3/006 |
| 9,915,834 | B2 * | 3/2018 | Qu | G02F 1/1309 |
| 2002/0135395 | A1 * | 9/2002 | Smith | G02F 1/1309 324/750.2 |
| 2007/0013408 | A1 * | 1/2007 | Hamamoto | G09G 3/006 324/754.03 |
| 2014/0292366 | A1 * | 10/2014 | Wang | G02F 1/1309 324/756.07 |
| 2018/0045988 | A1 * | 2/2018 | Li | G09G 3/00 |
| 2019/0066554 | A1 * | 2/2019 | Wang | G09G 3/006 |

* cited by examiner

LIGHTING-ON DEVICE AND METHOD FOR CELL TEST

CROSS REFERENCE

The present application is based upon and claims priority to Chinese Patent Application No. 201710111937.X, filed on Feb. 28, 2017, and the entire contents thereof are incorporated herein by reference.

TECHNICAL FIELD

At least one embodiment of the present disclosure relates to a lighting-on device and a method for cell test.

BACKGROUND

Lighting-on device, also known as probe unit (PU), is a precise probe component which is mounted probe device and used for applying signals to a display panel. The applied signals include data signal and gate signal. The lighting-on device is provided with a manipulator (MNP) and a lighting-on block, and the lighting-on block and the display panel are aligned accurately to perform lighting on. Lighting on signals are generated by a driving circuit of a printed circuit board (PCB), and are applied by the lighting-on block.

It is noted that the above disclosed information is merely used for readily understanding the background of the present disclosure, and thus the information that is not well-known to a person skilled in the art can be included herein.

SUMMARY

At least one embodiment of the present disclosure relates to a lighting-on device and a method for cell test.

At least one embodiment of the present disclosure provides a lighting-on device, including:

a movable unit including a first marker;

an image acquisition unit configured to acquire an image indicating an actual relative positional relationship between the first marker and a second marker on a display panel;

a calculation unit configured to calculate the actual relative positional relationship between the first marker and the second marker according to the image;

a first position adjustment unit configured to drive the movable unit so as to adjust the actual relative positional relationship; and a first control unit configured to determine whether the adjusted actual relative positional relationship has been aligned by the first position adjustment unit according to whether a difference between the actual relative positional relationship and a theoretical relative positional relationship between the first marker and the second marker that are properly aligned in theory exceeds a setting value.

At least one embodiment of the present disclosure provides a method for cell test with a lighting-on device, including:

aligning, by an aligning marker on a display panel, a plurality of probes of a movable unit of the lighting-on device with a plurality of pins of a pad area of the display panel, wherein the movable unit comprises a first marker;

applying, by the lighting-on device, a test signal to the display panel;

performing, by a testing apparatus, the cell test on the display panel;

when a plurality of continuous display panels are tested to be defective at an identical position during testing, moving an image acquisition unit to a second marker of the display panel corresponding to the position where a defect occurs in the display panel, to image the first marker and the second marker, so as to acquire an image indicating the actual relative positional relationship (Pa) between the first marker and the second marker; and determining whether a difference between the actual relative positional relationship (Pa) and a theoretical relative positional relationship (Pt) between the first marker and the second marker that are properly aligned in theory exceeds a setting value (S);

wherein, if the difference exceeds the setting value (S), the position of the movable unit is adjusted so as to realize a relationship condition of $|Pa-Pt| \leq S$, and if the difference does not exceed the setting value (S), continue to perform cell test on the next display panel, and if the same defect still occurs at the same position, the device alerts.

It is appreciated that the general description above and the detailed description as follow are exemplary and illustrative which do not intend to limit to the scope of the present disclosure.

The summary of the technical implementations and examples described in the present disclosure herein does not include the entire content of the present disclosure and does not equal to the whole scope to be protected of the present disclosure.

BRIEF DESCRIPTION OF THE DRAWINGS

The figures of the embodiments will be described simply for clearly explaining the technical solution of the embodiments of the present disclosure. It is apparent that the figures described as follow merely refer to some of the embodiments of the present disclosure, which do not intend to be limited thereto.

REFERENCE NUMBER

Figure 1:
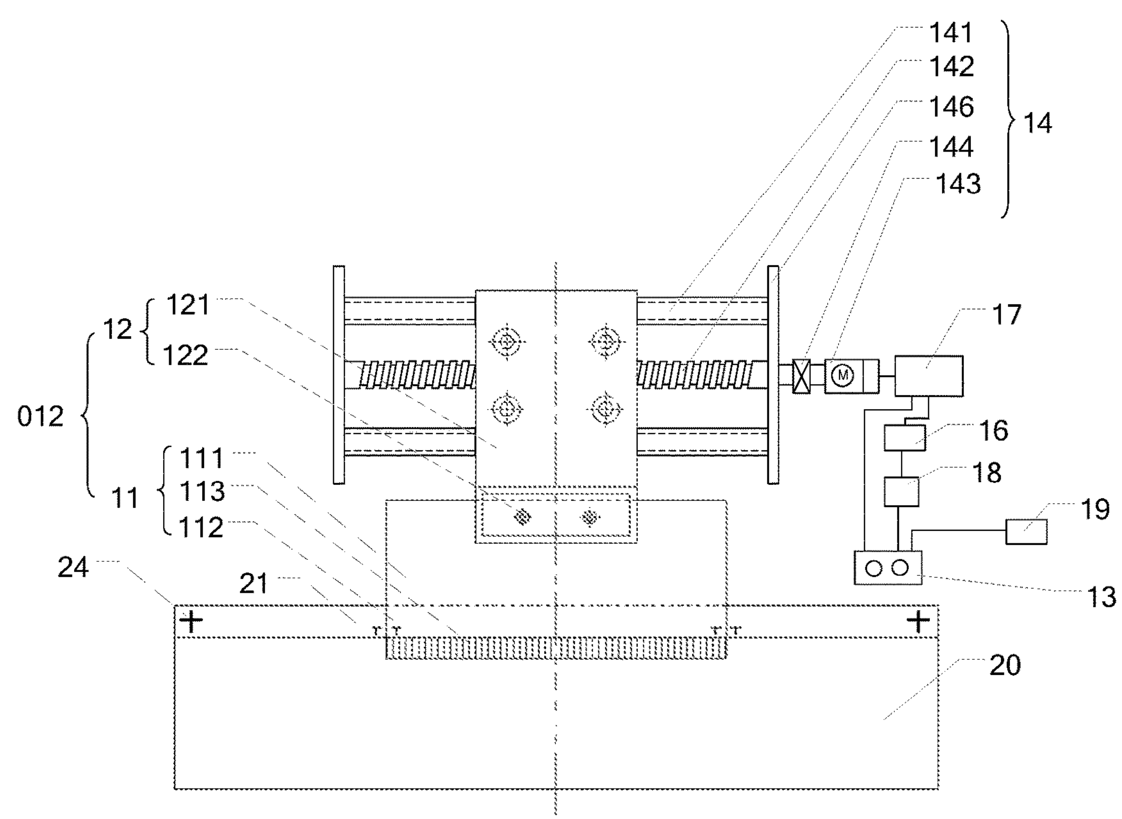
FIG. 1 is a plan view illustrating a lighting-on device used for cell test according an embodiment of the present disclosure.

10—base; 11—probe unit; 111—first body; 112—first marker; 113—probe; 12—carrier unit; 121—second body; 122—via; 123—fixing part; 13—image acquisition unit; 16—calculation unit; 17—first control unit; 18—first storage unit; 19—second control unit; 20—display panel; 21—second marker; 24—aligning marker; 22—pad area; 23—pin; 14—first position adjustment unit; 141—first slide rail; 142—screw; 1211—screw hole; 143—first servo motor; 144—coupling; 146—retainer; 25—turn knob; 15—second position adjustment unit; 151—second slide rail; 152—third slide rail; 153—second servo motor; 154—third servo motor.

DETAILED DESCRIPTION

Hereinafter, implementations of the embodiments of the present disclosure will be described clearly and completely with reference to the drawings of the embodiments of the present disclosure, to make the objectives, implementations and advantages of the embodiments of the present disclosure more clear. Obviously, rather than being all the embodiments, the described embodiments are only part of the embodiments of the present disclosure. All other embodiments available to those skilled in the art based on the described embodiments of the present disclosure will fall within the protection scope of the present disclosure.

Unless otherwise defined, all technical or scientific terms used herein are to be interpreted as customary in the art to which the present disclosure belongs. Terms such as “first”, “second”, and the like used in the description and the claims of the present disclosure do not indicate any order, quantity or importance, instead, they are used to distinguish different components. Likewise, terms such as “include” or “including” or the like refer to that the element or component presented before such terms covers one or more listed elements, components or the equivalent presented after such terms without excluding other elements or components. Terms such as “connect” or “connected with” or the like are not limited to physical or mechanical connection, but may include electrical connection, either directly or indirectly. Terms such as “upper”, “lower”, “left”, “right” and the like are used to indicate relative positional relations, and the relative positional relation will change correspondingly as the absolute position of the described object changes.

In the process of cell test, it is needed to be observe artificially whether the alignment between a plurality of probes on the probe unit of the lighting-on device and a plurality of pins in the pad area of the display panel is adequate during the cell test. In this case, the situation for alignment is complicated because of a large number of probes and pins. When a malposition occurs, the MNP is knocked several times by an engineer, which results in that the MNP is damaged, the flatness of the MNP is reduced, the accuracy and the stability of the test apparatus is decreased and the instability of lighting-on operation is increased, thereby the efficiency for testing defects to display panels by automated optical inspection (AOI) is affected and the workload for engineers and the damage for property are increased. In addition, in this case, the degree of automation and that of intelligence are quiet low, and engineers are required to perform knocking operation while observing the MNP, which is not convenient for engineers.

At least one embodiment of the present disclosure provides a lighting-on device, for example as shown in FIG. 1, including:

a movable unit 012 including a first marker 112;

an image acquisition unit 13 configured to acquire an image indicating an actual relative positional relationship between the first marker 112 and a second marker 21 on a display panel 20;

a calculation unit 16 configured to calculate the actual relative positional relationship between the first marker 112 and the second marker 21 according to the image;

a first position adjustment unit 14 configured to drive the movable unit 012 so as to adjust the actual relative positional relationship; and a first control unit 17 configured to determine a difference between the actual relative positional relationship and a theoretical relative positional relationship, to determine whether the difference exceeds a setting value, and to determine whether the adjusted actual relative positional relationship has been aligned by the first position adjustment unit 14 accordingly. The theoretical relative positional relationship is a positional relationship between the first marker and the second marker in the case where the first marker and the second marker are aligned correctly.

In the present disclosure, the “units” may be implemented as an entity having a physical or mechanical structure configured to implement corresponding functions. For example, the movable unit may be implemented as a structure having a spiral and a motor driving the spiral. However, the present disclosure is not limited thereto, the movable unit may also be implemented as a structure having a cylinder driven by liquid or air pressure. In one embodiment, for example, the image acquisition unit may be implemented as a camera. Also, in one embodiment, the units such as the calculation unit, the first control unit or the like may be implemented as a dedicated circuit, a logical circuit, an integrated circuit (IC), or the like. In a further embodiment, the above units may be implemented by a processor and a memory, wherein when the computer readable codes stored in the memory is executed on the processor, it may cause the processor to perform corresponding functions. Other units may be implemented in similar ways, which will not be repeated herein.

Figure 2:
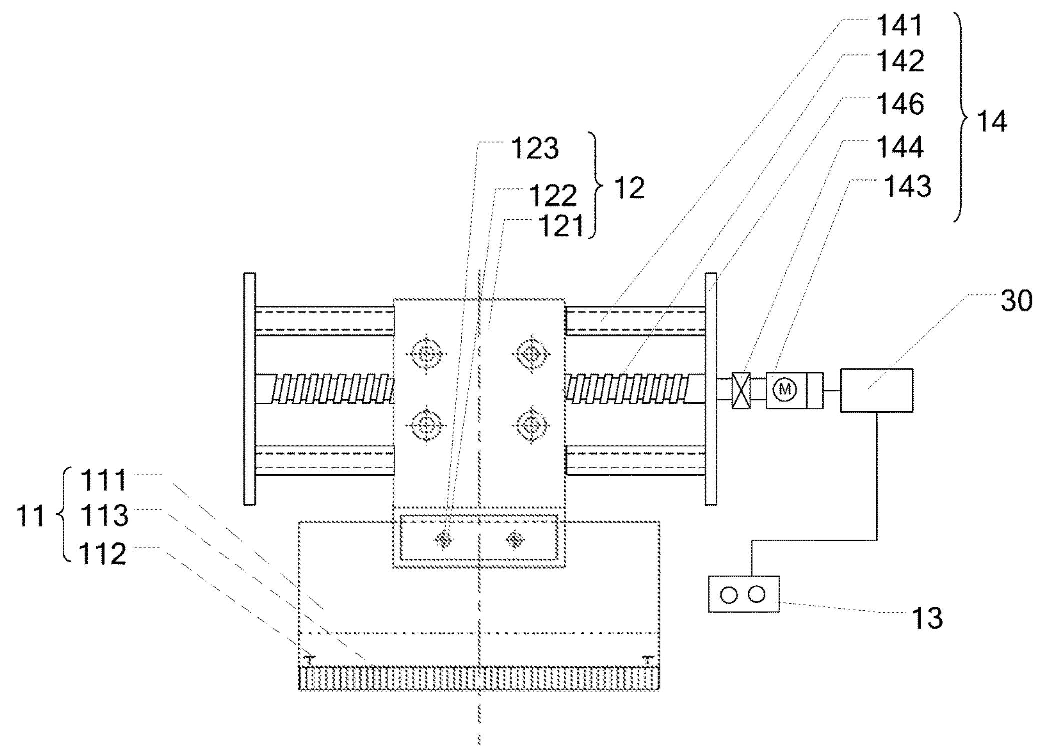
FIG. 2 is a plan view illustrating the lighting-on device according to the embodiment of the present disclosure.
Figure 3:
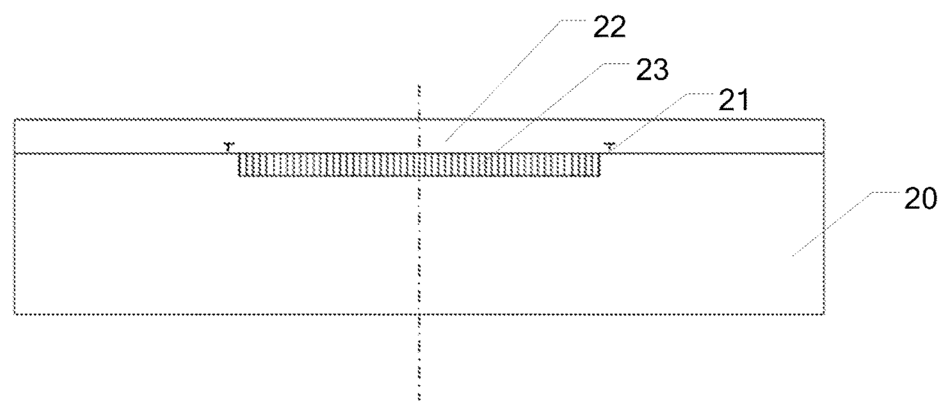
FIG. 3 is a plan view illustrating a pad area of a display panel according to the embodiment of the present disclosure.

FIGS. 2 and 3 show schematic diagrams indicating the separated lighting-on device and the separated display panel, respectively. During cell test, a plurality of probes 113 on the movable unit 012 of the lighting-on device and a plurality of pins 23 in a pad area 22 of the display panel correspond to each other one by one, such that signals can be applied to the display panel by the lighting-on device.

In the lighting-on device provided by the at least one of embodiments of the present disclosure, the step of observing the alignment between a plurality of probes 113 on the movable unit 012 of the lighting-on device and a plurality of pins 23 in the pad area 22 of the display panel is replaced by the step of observing the actual relative positional relationship between the first marker 112 on the probe unit 11 and a second marker 21 on a display panel 20, thereby, the operation is convenient and simple for engineers, the required data is easy to be acquire, the test speed is improved, the operation time is reduced and the accuracy for alignment is improved. For example, since the second marker 21 and the marker used by bonding the pins 23 in the pad area 22 with an external circuit may be the same one, there is no need to set an additional marker on the display panel. The external circuit may include a flexible circuit board (FPC) or a flexible chip on film (COF) such as driving IC.

According to an embodiment of the present disclosure, as shown in FIG. 1, the movable unit 012 further includes a probe unit 11 and a carrier unit 12. For example, the probe unit 11 includes a first body 111, and a first marker 112 and a plurality of probes 113 are disposed on the first body 111. For example, the carrier unit 12 includes a second body 121, and the second body 121 is configured to fix the first body 111.

According to the lighting-on device provided by an embodiment of the present disclosure, as shown in FIG. 1, the first position adjustment unit 14 are configured to drive the second body 121 to move the first body 111, such that the position of the first marker can be adjusted to adjust the actual relative positional relationship between the first marker 112 and the second marker 21.

According to the lighting-on device provided by an embodiment of the present disclosure, as shown in FIG. 1, the first marker 112 is fixed to the first body 11 and the second marker 21 is fixed to the display panel 20. For example, a plurality of probes 113 are fixed to the first body 111, which facilitates to change the alignment between the plurality of probes 113 and the plurality of pins 23 into the alignment between the first marker 112 and the second marker 21 because for example the relative positional relationship between the first marker 112 and the plurality of probes is maintained to be constant all the time.

According to the lighting-on device provided by an embodiment of the present disclosure, as shown in FIG. 1, the carrier unit 12 further includes a via 122 and a fixing part 123, and the via 122 is disposed on the second body 121 and the first body 111 is fixed on the second body 121 by the fixing part 123. For example, the fixing part includes a bolt and a nut and the embodiment does not intend to limit thereto.

According to the lighting-on device provided by an embodiment of the present disclosure, as shown in FIG. 1, two retainers are disposed on both sides of the first slide rail 141 respectively to define a slide area of the carrier unit 12.

Figure 5:
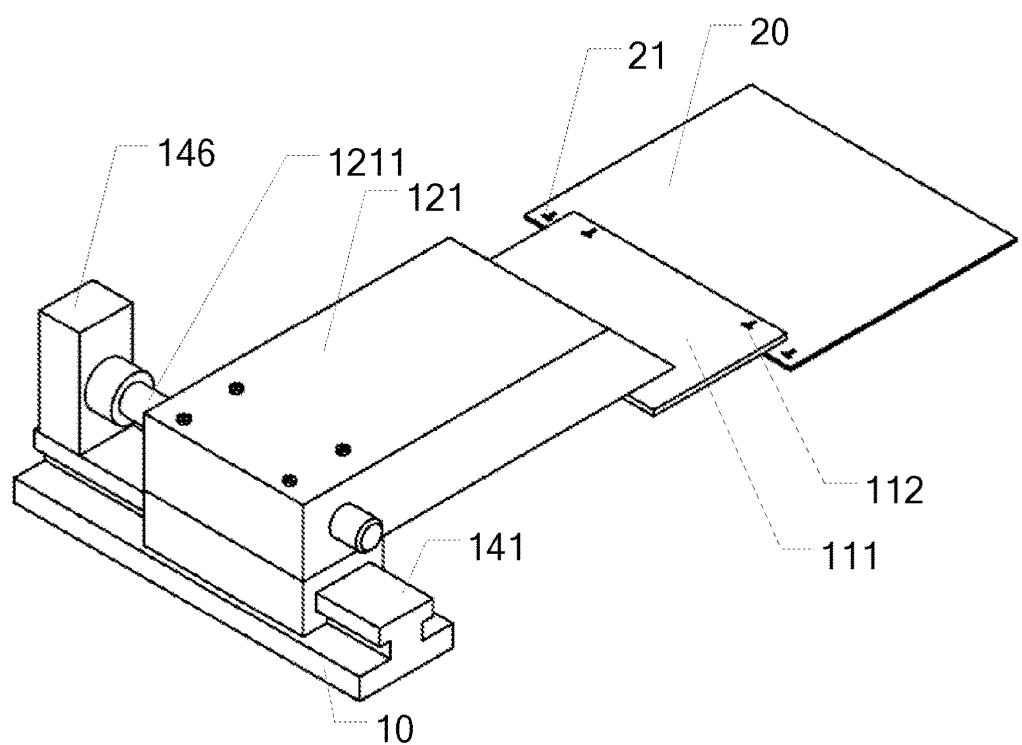
FIG. 5 is a perspective view illustrating the lighting-on device according to the embodiment of the present disclosure.
Figure 6:
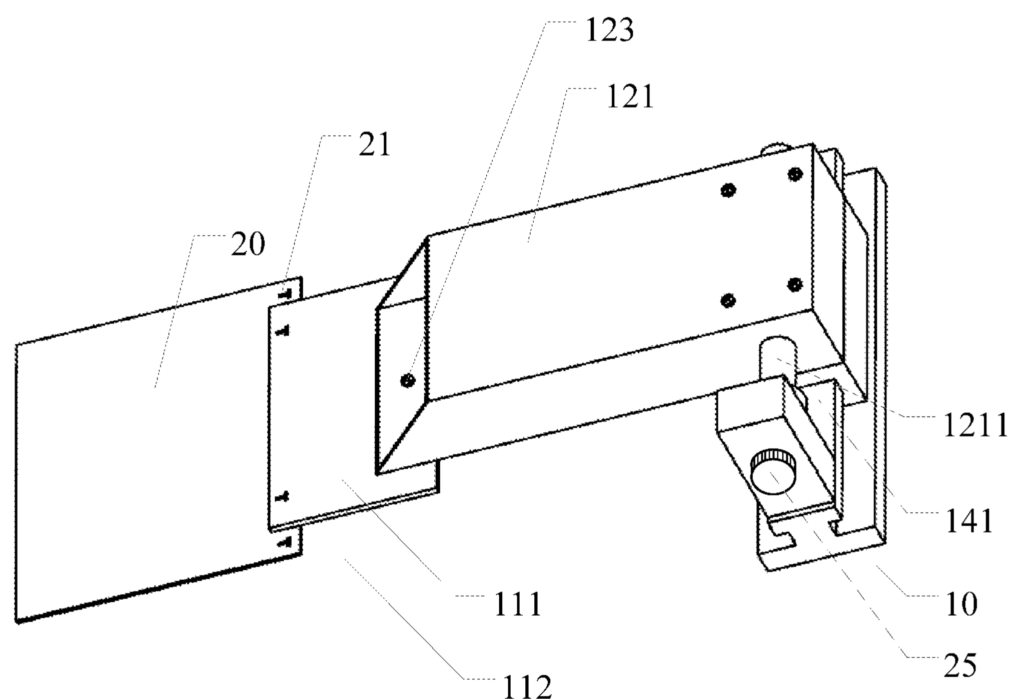
FIG. 6 is a perspective view illustrating the lighting-on device according to the embodiment of the present disclosure.

According to the lighting-on device provided by an embodiment of the present disclosure, as shown in FIG. 1, the lighting-on device further includes a base 20 (not shown in FIG. 1, but see FIG. 5). The first position adjustment unit 14 includes a first slide rail 141, a screw 142 and a screw hole 1211 (not shown in FIG. 1, but see FIG. 3). The first slide rail 141 and the screw 142 are disposed on the base 10. The screw hole 1211 is disposed on the carrier unit 12. The screw 142 passes through the screw hole 1211 and the screw may be rotated such that the carrier unit 12 is slid along the first slide rail 141. Since the screw structure is adopted between the screw (threaded rod) 142 and the carrier unit 12, the rotation of the screw can control the carrier unit 12 to go forward or backward, that is, the rotary motion of the screw 142 can be transformed into the linear motion of the carrier 142.

Figure 4:
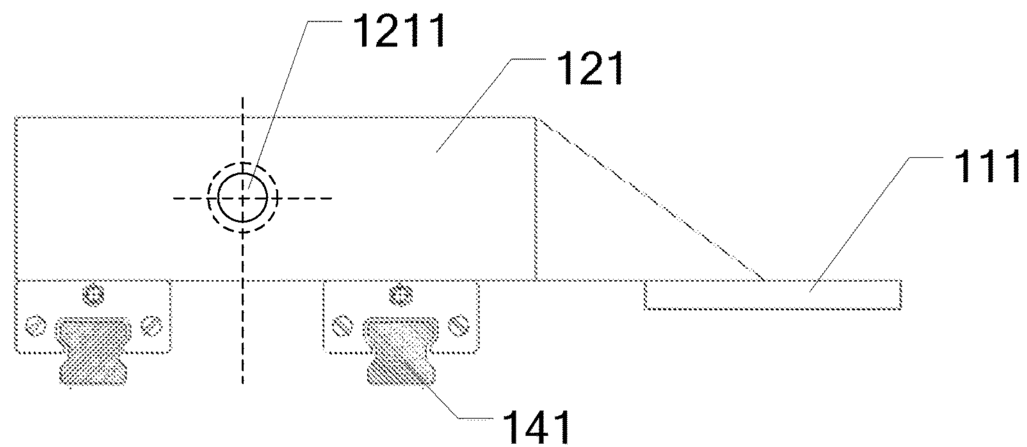
FIG. 4 is a front view illustrating the lighting-on device according to the embodiment of the present disclosure.

It is noted that FIGS. 1, 2 and 4 show two first slide rails (double slide rails) which cause that the carrier unit 12 could be slid more smoothly along the first slide rails 141. For example, the lighting-on device may also be provided with one first slide rail, as shown in FIG. 5 and the embodiment does not intend to limit to it.

According to the lighting-on device provided by an embodiment of the present disclosure, as shown in FIG. 1, the extension directions of the screw 142 and the first slide rail 141 are identical to reinforce the stability of slide of the carrier unit 12.

According to the lighting-on device provided by an embodiment of the present disclosure, as shown in FIG. 1, the first position adjustment unit 14 may further include a first servo motor 143 to allow the carrier unit 12 to be slid with an arbitrary distance as needed. The first servo motor 143 is connected to the screw 142 and configured to drive the screw 142 to rotate, for example, the first servo motor 143 is connected to the screw 142 through a coupling 144. The first servo motor 143 may transform electric energy into mechanical energy to rotate the screw 142, such that the carrier unit 142 may be slid along the first slide rail 141.

According to the lighting-on device provided by an embodiment of the present disclosure, as shown in FIG. 1, the first control unit 17 may be connected to the first servo motor 143 to realize automated control and the first control unit 17 may be configured to send an instruction to the first servo motor 143. For example, the image acquisition unit 13 acquires an image indicating an actual relative positional relationship between the first marker 112 and a second marker 21, the first storage unit 18 stores the image acquired by the image acquisition unit 13, the calculation unit 16 calculates the actual relative positional relationship between the first marker 112 and the second marker 21 according to the image, and the first control unit 17 sends an instruction to the first servo motor 143 according to the actual relative positional relationship, such that the movable unit 012 is moved by the first servo motor 143, for example, the screw 142 may be rotated by the first servo motor 143 to slide the carrier unit 12 along the first slide rail 141, the slide distance of the carrier unit 12 can be controlled by the first control unit 17. The lighting-on device provided by the embodiment does not require to knock the carrier unit, which causes that the stability of lighting-on operation is reinforced, components of the testing apparatus are prevented from being damage by manual operations, production cost is reduced and maintenance time and workload for engineers are reduced.

Figure 7:
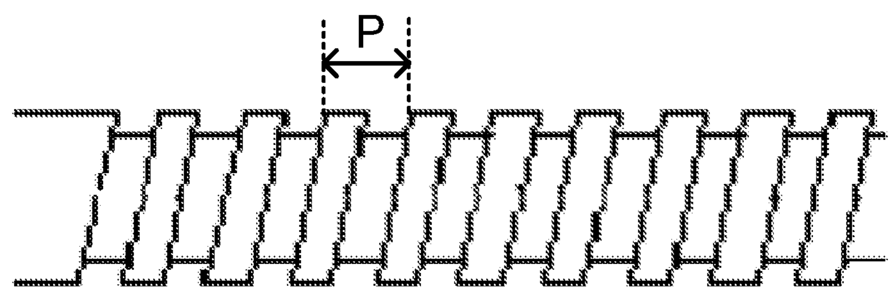
FIG. 7 is a schematic diagram illustrating a screw and a pitch of screw of the lighting-on device according to the embodiment of the present disclosure.

According to the lighting-on device provided by an embodiment of the present disclosure, as shown in FIG. 1, the first servo motor 143 is rotated a round such that the first position adjustment unit 14 disposed on the screw 142 is moved a distance of one pitch of the screw 142 along the first slide rail 141. For example, as shown in FIG. 7, the pitch P of the screw is about 450-550 μm. Generally, for example, since the pitch between the two adjacent probes is about 40 μm and the distance of which the first position adjustment unit 14 goes forward or backward while the screw is rotated a round is about 500 μm in the existing technology, one round of the rotation for the first servo motor 143 could be divided into 50 equal parts, each of which corresponds to the distance of 500 μm/50=10 μm, that is a quarter of the pitch between the two adjacent probes.

Figure 8:
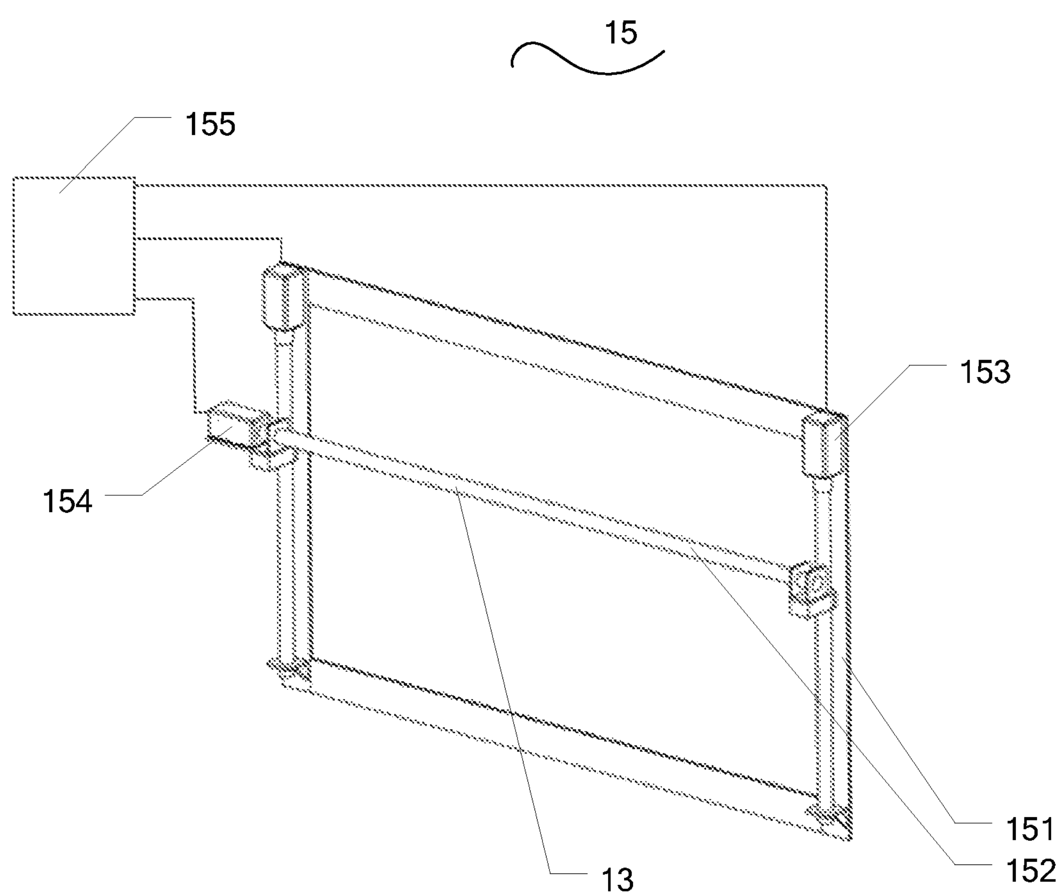
FIG. 8 is a schematic diagram illustrating a second position adjustment unit of the lighting-on device according to the embodiment of the present disclosure.

According to the lighting-on device provided by an embodiment of the present disclosure, as shown in FIG. 8, the screw 142 for example may be adjusted manually, and the lighting-on device includes a turn knob 25, which is connected to the screw 142. The screw 142 may be rotated by rotating the turn knob 25.

Figure 9:
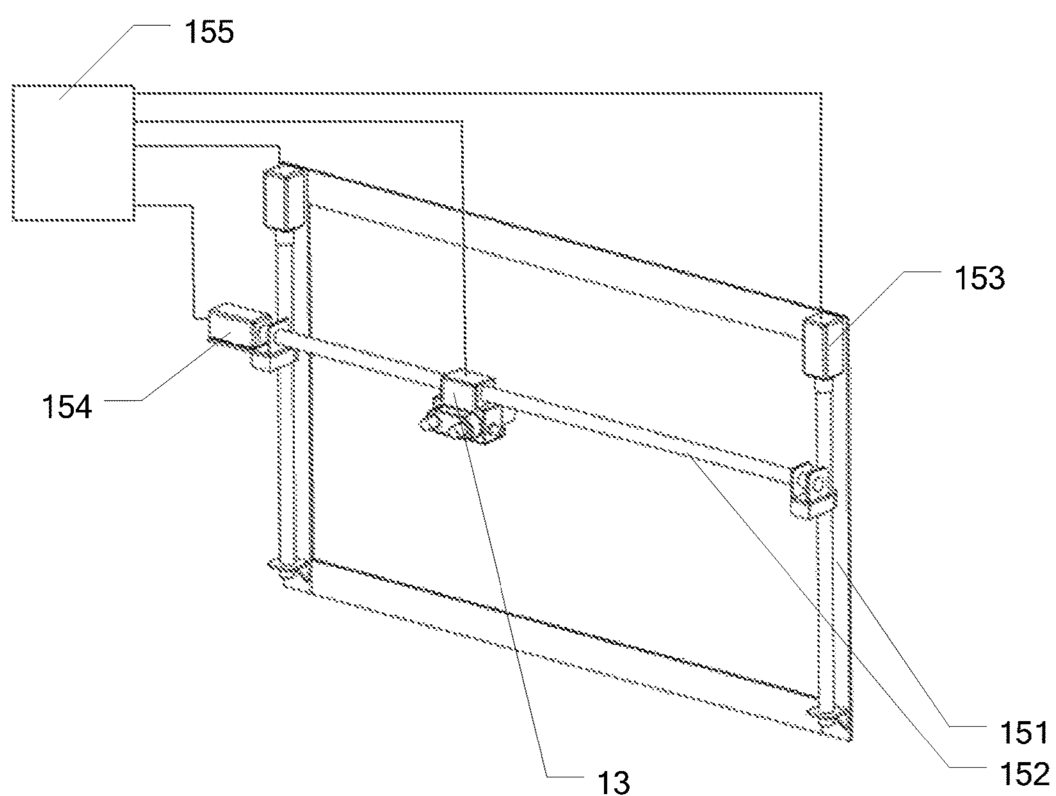
FIG. 9 is a schematic diagram illustrating the second position adjustment unit and an image acquisition unit of the lighting-on device according to the embodiment of the present disclosure.

According to the lighting-on device provided by an embodiment of the present disclosure, as shown in FIGS. 8 and 9, for facilitating the image acquisition unit to acquire the movement in a two dimensional plane, the lighting-on device further includes a second position adjustment unit configured to drive the image acquisition unit 13 to be moved in a two dimensional plane, the second position adjustment unit 15 includes a second slide rail 151 and a third slide rail 152, the third slide rail 152 is disposed on the second slide rail 151, and the third slide rail 152 is substantially perpendicular to the second slide rail 151 and the image acquisition unit 13 is disposed on the third slide rail 152. For example, the image acquisition unit 13 may be a camera.

According to the lighting-on device provided by an embodiment of the present disclosure, as shown in FIGS. 8 and 9, for more easily and accurately acquiring the actual relative positional relationship between the first marker 112 and the second marker 21, the lighting-on device may further include a second control unit 19, and the second position adjustment unit 15 may further include a second servo motor 153 and a third servo motor 154. The second servo motor 153 is connected to the second slide rail 151 and the third servo motor 154 is connected to the third slide rail 152. Each of the second slide rail 151 and the third slide rail 152 includes a screw and each of the second servo motor 153 and the third servo motor 154 is connected to the second control unit 19, and the second control unit 19 is configured to send an instruction to each of the second servo motor 153 and the third servo motor 154. For example, the second servo motor 153 and the third servo motor 154 may transform electric energy into mechanical energy. The speed and the direction of the movement for the image acquisition unit 13 and the terminate position of the image acquisition unit 13 can be controlled by the second control unit 19. It is noted that it is possible to omit the second control unit.

According to the lighting-on device provided by an embodiment of the present disclosure, as shown in FIG. 9, the image acquisition unit 13 for example may be connected to the second control unit 19, thus the image acquisition unit 13 could be automatically controlled by the second control unit 19 to be terminated at the desired position, such that the image corresponding to the desired position is acquired.

For example, the functions of the calculation unit 16, the first control unit 17, the first storage unit 18 and the second control unit 19 may be realized by one or more computers. Such a computer for example may be a general computing device or a dedicated computing device.

According to the lighting-on device provided by an embodiment of the present disclosure, in the case of which the functions of the calculation unit 16, the first control unit 17, the first storage unit 18 and the second control unit 19 may be realized by one or more computers, the alignment between the probe unit 11 and the pad area can be performed by the lighting-on device quickly and accurately, which results in that the operation time is reduced and the accuracy for alignment is improved, and without knocking the carrier unit, the stability of lighting-on operation is reinforced, components of the testing apparatus are prevented from being damage by manual operations, production cost is reduced and maintenance time and workload for engineers are reduced.

According to the lighting-on device provided by an embodiment of the present disclosure, as shown in FIG. 1, the first markers 112 may be respectively disposed on both sides of the first body 111 which are opposite to each other, or the first markers 112 may be disposed in other manner, the present disclosure does not intend to limit to it. For example, a first marker 112 is disposed on one side of the first body 111. In the figures of the present disclosure, embodiments of the present disclosure will be described by the example of which the first marker 112 and the second marker 21 have a shape of "T". For example, an aligning marker 24 may be disposed on the display panel to facilitate the alignment between the plurality of probes on the movable unit of the lighting-on device and the plurality of pins in the pad area of the display panel.

The first servo motor 143, the second servo motor 153 and the third servo motor 154 may be rotated clockwise or counterclockwise. For example, the clockwise and counterclockwise rotation of the above servo motors may be performed by receiving a computer (the first control unit 17 or the second control unit 19) instruction.

Figure 10:
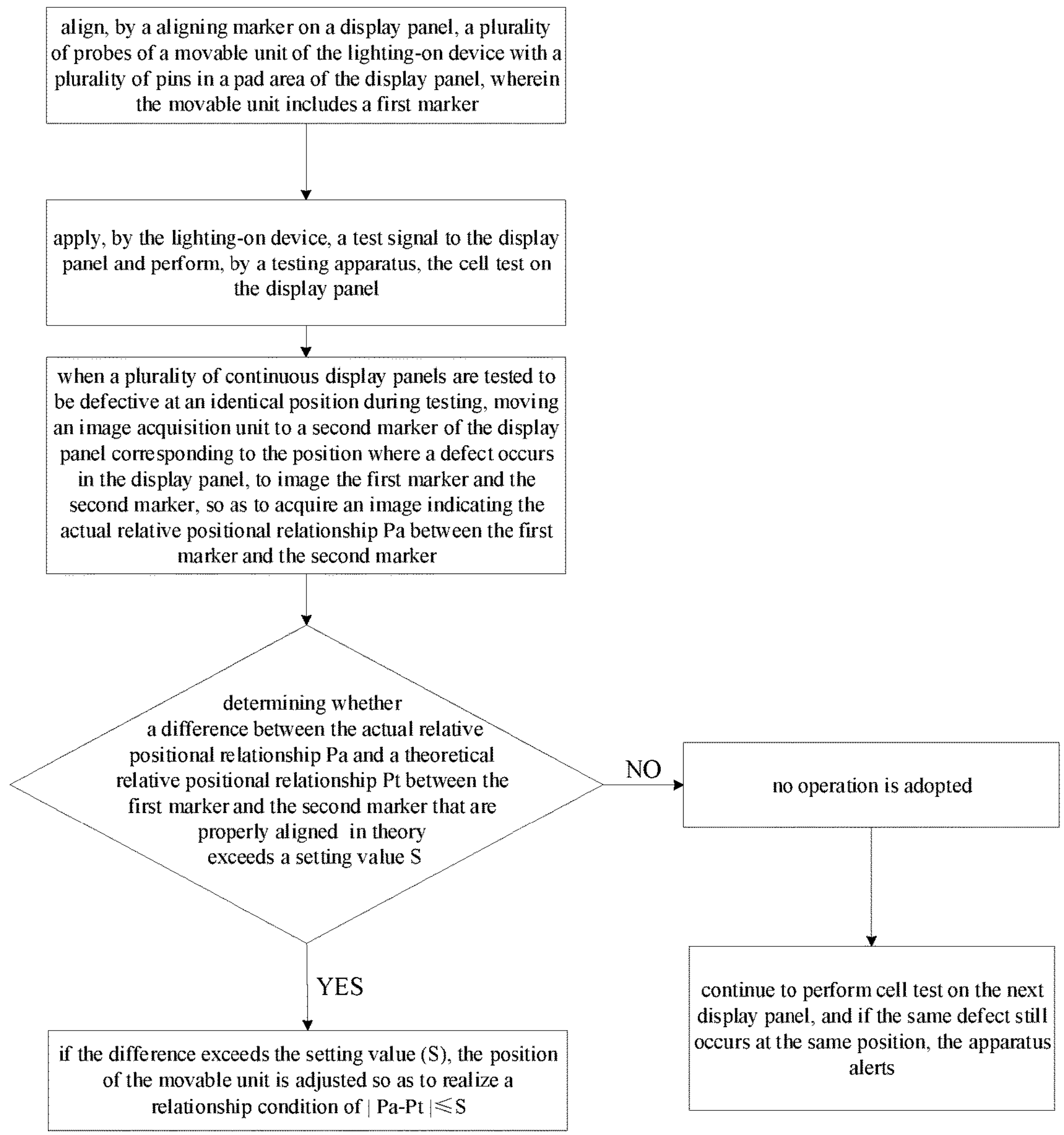
FIG. 10 is a flow chart of a method for cell test according to an embodiment of the present disclosure.

At least one embodiment of the present disclosure provides a method for cell test with a lighting-on device, as shown in FIG. 10 including:

aligning, by an aligning marker 24 on a display panel 20, a plurality of probes 113 of a movable unit 012 of the lighting-on device with a plurality of pins 23 of a pad area 22 of the display panel 20, wherein the movable unit 012 comprises a first marker 112;

applying, by the lighting-on device, a test signal to the display panel 20;

performing, by a testing apparatus, the cell test on the display panel 20;

when a plurality of continuous display panels (for example, 3 display panels) are tested to be defective at an identical position during testing, for example, pin miss which may occur when the relative position relationship is deviated, pausing the test and moving an image acquisition unit 13 to a second marker 21 of the display panel corresponding to the position where a defect occurs in the display panel, to image the first marker 112 and the second marker 21, so as to acquire an image indicating the actual relative positional relationship (Pa) between the first marker 112 and the second marker 21; and determining whether a difference between the actual relative positional relationship Pa and a theoretical relative positional relationship Pt between the first marker 112 and the second marker 21 that are properly aligned in theory exceeds a setting value S;

wherein, if the difference exceeds the setting value S, the position of the movable unit is adjusted so as to realize a relationship condition of $|Pa-Pt| \leq S$, and if the difference does not exceed the setting value (S), continue to perform cell test on the next display panel, and if the same defect still occurs at the same position, the device alerts.

According to the method for cell test provided by an embodiment of the present disclosure, the movable unit 012 may be adjusted by the first control unit 17 to perform automated control.

Form example, the image acquired by the image acquisition unit 13 is stored in a first storage unit 18, and a first calculation unit 16 calculates the actual relative positional relationship P1 between the first marker 112 and the second marker 21 according to the image.

According to the method for cell test provided by an embodiment of the present disclosure, the image acquisition unit is moved to the second marker 21 of the display panel 20 by a second control unit 19, according to a coordinate of the second marker 21, to perform automated control.

For example, the actual relative positional relationship may include a distance and/or an angle and the embodiments of the present disclosure are described by the example in which a distance is the actual relative positional relationship. For example, the distance D may be constant and $|L-D|$ may vary depending on the changes of the actual distance L. In an embodiment, D may vary depending on the changes of the size of the display panel. For example, in order to acquire the actual distance between the first marker 112 and the second marker 21 more accurately, D is less than or equal to a half of the distance between the two adjacent pins 23 in the pad area 23 of the display panel or a half of the distance between the two adjacent probes 113 of the probe unit 11.

According to the method for cell test provided by an embodiment of the present disclosure, the step of which the alignment between a plurality of probes 113 on the probe unit 11 of the lighting-on device and a plurality of pins 23 in the pad area 22 of the display panel is observed is replaced by the step of which the actual relative positional relationship between the first marker 112 on the probe unit 11 and a second marker 21 on a display panel 20 is observed, thereby, the operation is convenient and simple for engineers, the required data is easy to be acquire and the test speed is improved.

The deviation between the probes 113 on the movable unit 012 (the probe unit 11) and the pins 23 in the pad area 22 may be acquired by the difference between the actual distance L between the first marker 112 on the movable unit 012 and the second marker 21 on the display panel 20 and a distance D between the first marker 112 and the second marker 21 in the time of which the alignment is adequate in theory.

According to the method for cell test provided by an embodiment of the present disclosure, the actual distance L between the first 112 and the second marker 21 on the display panel 20 may be acquired by imaging the display panel 20 which a defect occurs and the movable unit 012 (the probe unit 11) which sends a test signal to the display panel 20 and checking the images thereof.

According to the method for cell test provided by an embodiment of the present disclosure, the first slide rail 141 and the screw 142 are disposed on the base 10 and the carrier unit 12 is provided with the screw hole 1211, the screw 142 passes through the screw hole 1211, and the screw 142 is rotated such that the carrier unit 12 is slid along the first slide rail 141.

According to the method for cell test provided by an embodiment of the present disclosure, the first servo motor 143 is connected to the screw 142 such that the first servo motor 143 is configured to drive the screw 142 to rotate.

According to the method for cell test provided by an embodiment of the present disclosure, the first control unit 17 is connected to the first servo motor 143 such that the first control unit 17 is configured to send an instruction to the first servo motor 143. The slide distance of the carrier unit 12 can be controlled by the first control unit 17, and the acquired images can be stored in the form of pictures, for example, the images may be stored in the first storage unit 18. The first control unit 17 may determine the actual distance between the first marker 112 and the second marker 21 according to the pictures stored in the first storage unit 18 and send an instruction to the first servo motor 143.

According to the method for cell test provided by an embodiment of the present disclosure, the method may further include moving the image acquisition unit 13 in a two dimensional plane, and the step of moving the image acquisition unit 13 in a two dimensional plane includes the following steps.

A second slide rail 151 and a third slide rail 152 are provided, the third slide rail 152 is disposed on the second slide rail 151, and the third slide rail 152 is substantially perpendicular to the second slide rail 151 and the image acquisition unit 13 is disposed on the third slide rail 152.

The second servo motor 153 is connected to the second slide rail 151 and the third servo motor 154 is connected to the third slide rail 152, each of the second slide rail 151 and the third slide rail 152 includes a screw 142 and each of the second servo motor 153 and the third servo motor 154 is connected to the second control unit 19, such that the second control unit 19 is configured to send an instruction to each of the second servo motor 153 and the third servo motor 154.

According to the method for cell test provided by an embodiment of the present disclosure, the method may include the following steps:

(1) when three continuous display panels are tested to be defective at an identical position in AOI (automated optical inspection) test, pausing the AOI apparatus;

(2) sending, by a computer, an instruction to the image acquisition unit 13; after receiving the instruction, moving the image acquisition unit 13 to the position of the movable unit 012 corresponding to the position where a defect occurs; imaging the first marker 112 on the movable unit 012 and the second marker 21 on the display panel 20; and feeding the image information back to the computer;

(3) checking, by the computer, the actual distance L between the first marker 112 and the second marker 21; and comparing, by the computer, the actual distance L with the theoretical distance D between the first marker 112 and the second marker 21 in the time of which the alignment is adequate in theory to acquire the difference;

(4) determining, by the computer, whether the difference between the actual L and the theoretical distance D exceeds a setting value S;

a. if the difference between the actual L and the theoretical distance D exceeds a setting value S, sending, by the computer, the instructing to the first servo motor; the carrier unit 12 going forward or backward by rotation of the first servo motor with a certain angle, such that the probe unit 11 is moved to realize a relationship condition of L-D 1≤S, for example, when the relationship condition is realized as L=D, the lighting-on operation resuming and the AOI apparatus being activated again;

if the difference between the actual L and the theoretical distance D does not exceed the setting value S, the AOI apparatus being activated again; and if the same defect still occurs at the same position, the apparatus alerting, and artificially addressing, by engineers, the abnormality of the apparatus.

Figure 11:
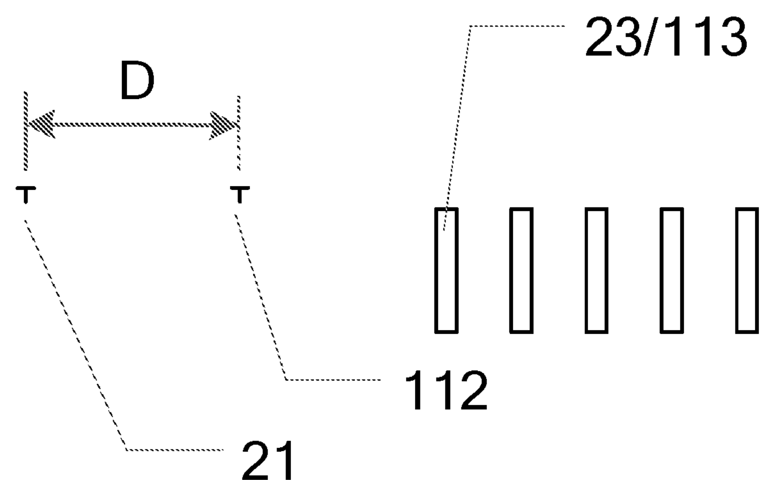
FIG. 11 is a schematic diagram illustrating a distance D between a first marker 112 to a second marker 21 that are properly aligned in theory in the method for cell test according to the embodiment of the present disclosure.
Figure 12:
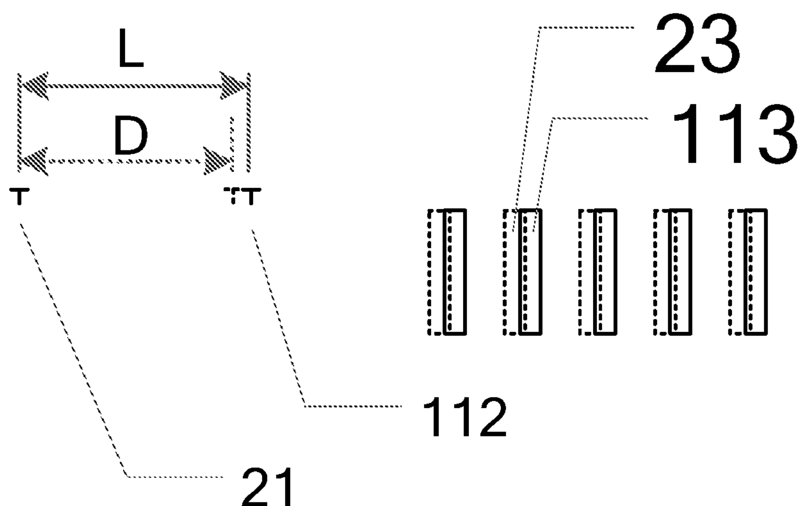
FIG. 12 is a schematic diagram illustrating the actual distance L between a first marker 112 on a probe unit 11 to a second marker 21 on the display panel 20 in the method for cell test according to the embodiment of the present disclosure.

For example, the distance D between the first marker 112 and the second marker 21 in the time of which the alignment is adequate in theory is shown in FIG. 11 and the actual distance L between the first marker 112 on the probe unit 11 and the second marker 21 on the display panel 20 is shown in FIG. 12.

It is noted that embodiments of the present disclosure do not limit to the numerical value of the setting value. For example, the setting value may be determined according to the width of each of a probe and a pin, the pitch between the two adjacent probes or the pitch between the two adjacent pins, and the width of each of a probe and a pin is for example a width along a direction perpendicular to the extension directions of the probes and the pins. For example, the setting value is less than the width of a probe 113 and the pitch between the two adjacent probes, or the setting value is less than the width of a pin 23 and the pitch between the two adjacent pins. In an embodiment, in order to apply signals more smoothly, the setting value may be less than a half of the width of a pin 113 or a half of the width of a pin 23. In another embodiment, in order to increase the contact area between the probes and the pins to facilitate the applying of signals, the setting value may be less than a quarter of the width of a probe 113 or a quarter of the width of a pin 23. In still another embodiment, the width of a probe 113 is approximately equal to the pitch between the two adjacent probes and the width of a pin 23 is approximately equal to the pitch between the two adjacent pins, to which embodiments of the present disclosure do not limited. Moreover, since the setting value is an absolute value of the difference between two numerical value, the setting value is greater than or equal to zero.

There are several matters should be noted as follow.

(1) In embodiments and figures of the present disclosure, the same reference number refers to the same element or component unless otherwise defined.

(2) In embodiments and figures of the present disclosure, the structure herein merely relates to the structure described in embodiments of the present disclosure, and other structure may refer to generally designs.

(3) For clarity, the thickness of the layer or area is exaggerated in the figures of the present disclosure. For example, it is appreciated that one element such as a layer, a film, an area or a substrate can be directly "on" or "under" other element or there are one or more intervening elements between the one element and the other element when the one element are referred to be "on" or "under" the other element.

(4) The features in the same embodiment or the different embodiments of the present disclosure can be combined in any appropriate way if they are not conflicting with each other.

Hereinabove are merely optional implementations of the present disclosure and the scope to be protected of the present disclosure is not limited to it. It should be noted that various improvements and alternatives are possible to those ordinary skilled in the art without departing from the technical principle of the present disclosure. All these improvements and alternatives will also fall into the protection scope of the present disclosure, and the protection scope of the present disclosure is defined as the appended claims.

What is claimed is:

1. A lighting-on device, comprising:

a movable unit comprising a first marker;

an image acquisition unit, configured to acquire an image indicating an actual relative positional relationship between the first marker and a second marker on a display panel;

a calculation unit, configured to calculate the actual relative positional relationship between the first marker and the second marker according to the image;

a first position adjustment unit, configured to drive the movable unit so as to adjust the actual relative positional relationship; and a first control unit, configured to determine whether the adjusted actual relative positional relationship has been aligned by the first position adjustment unit according to whether a difference between the actual relative positional relationship and a theoretical relative positional relationship between the first marker and the second marker that are properly aligned in theory exceeds a setting value.

2. The lighting-on device according to claim 1, further comprising a first storage unit, wherein the image acquisition unit is connected to the first storage unit, and the first storage unit is configured to store the image acquired by the image acquisition unit.

3. The lighting-on device according to claim 1, wherein the movable unit further comprises a probe portion comprising a plurality of probes and a carrier portion configured to fix the probe portion, and the first marker is disposed on the probe portion; and wherein the first position adjustment unit is configured to drive the carrier portion to move the probe portion, so as to adjust the actual relative positional relationship between the first marker and the second marker.

4. The lighting-on device according to claim 3, further comprising a base, wherein the first position adjustment unit comprises a first slide rail, a screw and a screw hole, the first slide rail and the screw are disposed on the base and the carrier unit is provided with the screw hole, the screw passes through the screw hole, and the screw is rotated such that the carrier unit is slid along the first slide rail.

5. The lighting-on device according to claim 4, wherein the extension directions of the screw and the first slide rail are identical.

6. The lighting-on device according to claim 3, wherein the first position adjustment unit further comprises a first servo motor, and the first servo motor is connected to the screw and is configured to drive the screw to rotate.

7. The lighting-on device according to claim 6, wherein the first control unit is connected to the first servo motor and configured to send an instruction to the first servo motor.

8. The lighting-on device according to claim 1, further comprising a second position adjustment unit, wherein the second position adjustment unit is configured to drive the image acquisition unit to be moved in a two dimensional plane, the second position adjustment unit comprises a second slide rail and a third slide rail, the third slide rail is disposed on the second slide rail, and the third slide rail is substantially perpendicular to the second slide rail and the image acquisition unit is disposed on the third slide rail.

9. The lighting-on device according to claim 8, further comprising a second control unit, wherein the second position adjustment unit further comprises a second servo motor and a third servo motor, the second servo motor is connected to the second slide rail and the third servo motor is connected to the third slide rail, each of the second slide rail and the third slide rail comprises a screw and each of the second servo motor and the third servo motor is connected to the second control unit, and the second control unit is configured to send an instruction to each of the second servo motor and the third servo motor.

10. The lighting-on device according to claim 1, wherein the first marker is fixed on the movable unit and the second marker is fixed on the display panel.

11. A method for cell test with a lighting-on device, comprising:

aligning, by an aligning marker on a display panel, a plurality of probes of a movable unit of the lighting-on device with a plurality of pins in a pad area of the display panel, wherein the movable unit comprises a first marker;

applying, by the lighting-on device, a test signal to the display panel;

performing, by a testing apparatus, the cell test on the display panel;

when a plurality of continuous display panels are tested to be defective at an identical position during testing, moving an image acquisition unit to a second marker of the display panel corresponding to the position where a defect occurs in the display panel, to image the first marker and the second marker, so as to acquire an image indicating the actual relative positional relationship (Pa) between the first marker and the second marker; and determining whether a difference between the actual relative positional relationship (Pa) and a theoretical relative positional relationship (Pt) between the first marker and the second marker that are properly aligned in theory exceeds a setting value (S);

wherein, if the difference exceeds the setting value (S), the position of the movable unit is adjusted so as to realize a relationship condition of $|Pa-Pt| \leq S$, and if the difference does not exceed the setting value (S), continue to perform cell test on the next display panel, and if the same defect still occurs at the same position, the apparatus alerts.

12. The method according to claim 11, wherein the movable unit is adjusted by a first control unit to perform automated control.

13. The method according to claim 12, wherein the image acquired by the image acquisition unit is stored in a first storage unit, and a first calculation unit calculates the actual relative positional relationship (Pa) between the first marker and the second marker according to the image.

14. The method according to claim 11, wherein, according to a coordinate of the second marker, the image acquisition unit is moved to the second marker of the display panel by a second control unit, to perform automated control.

* * * * *